United States Patent [19]

Tomlinson, Jr. et al.

[11] Patent Number: 5,212,667

[45] Date of Patent: May 18, 1993

[54] LIGHT IMAGING IN A SCATTERING MEDIUM, USING ULTRASONIC PROBING AND SPECKLE IMAGE DIFFERENCING

[75] Inventors: Harold W. Tomlinson, Jr., Scotia; Jerome J. Tiemann, Schenectady, both of N.Y.

[73] Assignee: General Electric Company, Schenectady, N.Y.

[21] Appl. No.: 829,668

[22] Filed: Feb. 3, 1992

[51] Int. Cl.$^5$ .............................. G03B 42/06
[52] U.S. Cl. ............................... 367/7; 367/11
[58] Field of Search ............... 367/7, 11, 100; 364/413.25; 128/660.01

[56] References Cited

U.S. PATENT DOCUMENTS

| 4,180,790 | 12/1979 | Thomas | 367/7 |
| 4,271,684 | 8/1990 | Brisken et al. | 29/25.35 |
| 4,425,525 | 1/1984 | Smith et al. | 310/336 |
| 4,460,841 | 7/1984 | Smith et al. | 310/334 |
| 4,471,349 | 9/1984 | Strolle | 340/727 |

FOREIGN PATENT DOCUMENTS 8900278  1/1989  European Pat. Off. .

OTHER PUBLICATIONS

Jarry et al., "Simulation of Laser Tomoscopy in a Heterogeneous Biological Medium", Medical & Biological Engineering & Computation, 1986, 24, 407–414.
Takiguchi et al., "Laser Pulse Tomography Using a Streak Camera", Proceedings Image Detection and Quality, Jul. 1986, pp. 147–150.
S. Andersson-Engels et al., "Time-Resolved Transillumination for Medical Diagnostics", Optics Letters, vol. 15, No. 21, Nov. 1990, pp. 1179–1181.

Primary Examiner—Daniel T. Pihulic
Attorney, Agent, or Firm—Marvin Snyder

[57] ABSTRACT

Coherent light is projected through a scattering medium. The light emerging from the medium is a superposition of a multitude of scattered wavelets, each of which represents a specific scattering path. These wavelets are projected onto a diffuse reflecting surface (the viewing plane of a two-dimensional photodetector array) where they interfere with each other, giving rise to a speckle pattern. By introducing a focused ultrasound pulse into the medium, the position of the scatterers are changed at a known location (probe region) in the medium, and this causes a change in the speckle pattern. By comparing speckle images before and after the scatterers are moved, the light absorption properties of the probe region can be measured even though multiple scattering interferes with direct imaging of the region.

9 Claims, 2 Drawing Sheets

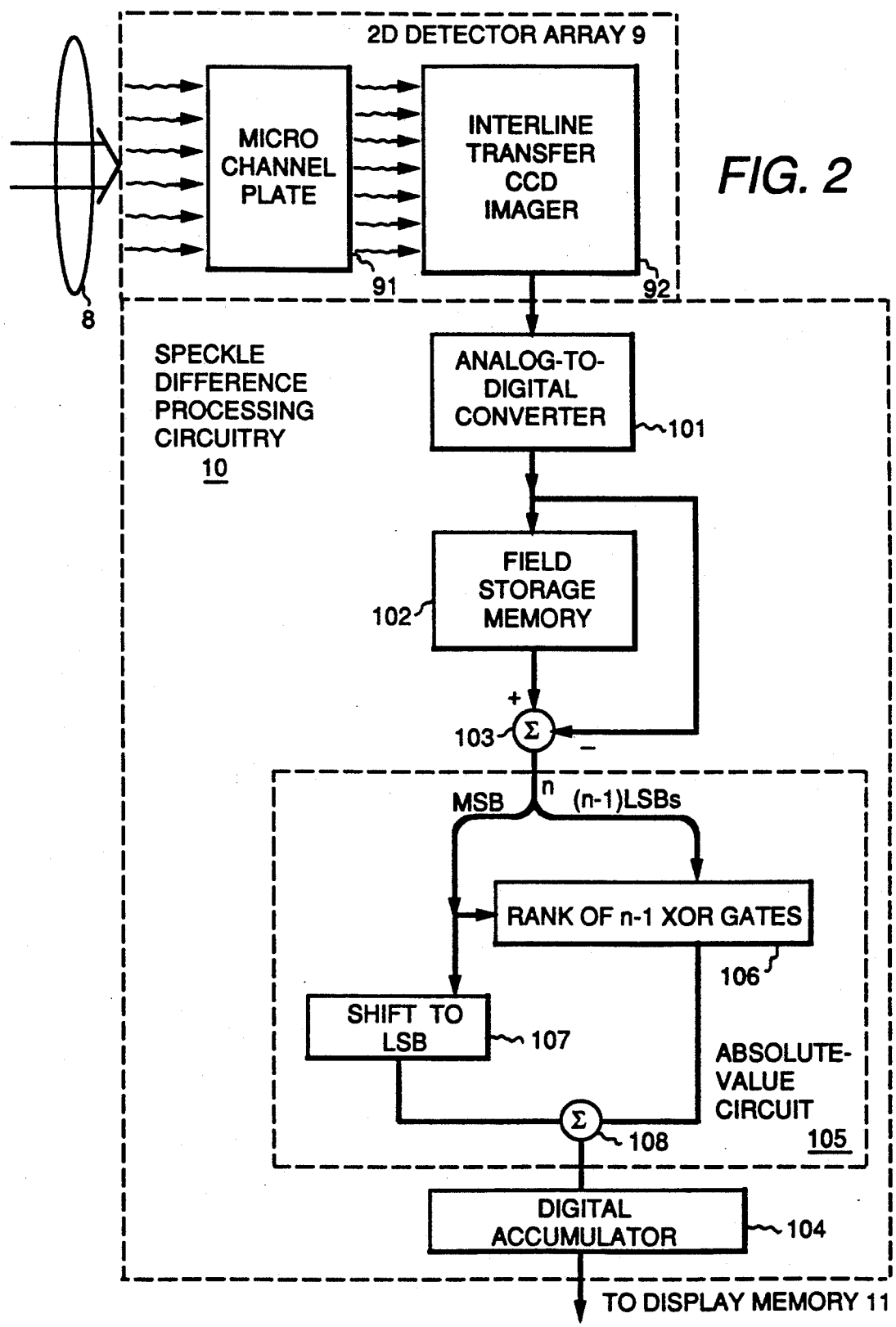

LIGHT IMAGING IN A SCATTERING MEDIUM, USING ULTRASONIC PROBING AND SPECKLE IMAGE DIFFERENCING

The invention relates to imaging in a densely scattering medium as relates, for example, to "transillumination" or "visible light tomography" systems to be used for medical imaging.

BACKGROUND OF THE INVENTION

These systems are under study with a goal of providing useful images of structures deep within the body without the use of ionizing radiation. There are at least three ways researchers have been trying to image in densely scattering media:

One way to image in a densely scattering medium is by measuring the time-of-flight of photons which travel in the medium and detecting those photons with the shortest travel time. Photons which experience multiple scattering well outside the beam path have a longer time-of-flight and can therefore be rejected. This technique has been suggested by Jarry et al. in their paper "Simulation of Laser Tomoscopy in a Heterogeneous Biological Medium", *Medical & Biological Engineering & Computation*, 1986, 24,407–414). This technique has been implemented by Takiguchi et al. as described in their paper "Laser Pulse Tomography Using a Streak Camera", *Proceedings Image Detection and Quality*, July 1986, and by S. Andersson-Engels et al. as described in their paper "Time-resolved Transillumination for Medical Diagnostics", *Optics Letters*, Vol. 15, No. 21, November, 1990. It requires sophisticated pulsed lasers, with pulse times in the picosecond to femtosecond range, and a very fast detection system. With time-of-flight systems, image resolution can be improved at the expense of signal strength.

A second way to image in a densely scattering medium uses coherent light illumination and optical heterodyning detection to reject scattered light. Because of the angular response of a heterodyned detector, it can be made sensitive only to light which exits the tissue normal to the detector axis. This technique will reject scattered light, but the technique suffers from very low signal strength, since the amount of coherent light in the medium falls off exponentially with the medium thickness. This technique has been demonstrated by researchers at the Thomson CGR research labs and by M. Toida et al. in the Inaba Biophoton Project, Japan. When applied to tissue imaging, the heterodyne and time-of-flight detection techniques are limited to imaging through about 2–3 cm tissue owing to the low signal levels of the system.

A third way to image in a densely scattering medium uses an optically heterodyned detector in conjunction with sound waves projected into the medium. A system of this type is described by Dolfi and Micheron of General Electric CGR SA in International Publication WO 89/00278 published on the base of the Patent Cooperation Act and entitled "IMAGING PROCESS AND SYSTEM FOR TRANSILLUMINATION WITH PHOTON FREQUENCY MARKING". Dolfi and Micheron use the fact that a sound wave projected into the medium causes the scatterers in the medium to vibrate. Light which is scattered by the medium therefore picks up a Doppler shift equal to the medium's vibration frequency. Dolfi and Micheron detect variations in the intensity of this Doppler shift by heterodyning the Doppler modulated light passing through the medium with unmodulated light, then selecting for the Doppler shift frequencies with electronic filters. Despite the directionality of the optical heterodyning procedures employed by Dolfi and Micheron, subsequent scattering in other portions of the scattering medium can undesirably interfere with direct imaging of the Doppler modulated light; Dolfi and Micheron describe ways to reduce this interference. These methods reduce the interference attributable to elastic scattering effects in the medium, but inelastic scattering effects in the medium can still introduce undesirable interference with direct imaging. Furthermore, since the number of photons which travel relatively straight after initial scattering is a negligible fraction of the total number of initially scattered photons, detection sensitivity tends to be poor if subsequently scattered photons remain undetected.

This invention concerns improving the measurement of light absorption in a localized region within a medium where multiple scattering dominates without rejecting multiply scattered light. Light imaging in such a medium is difficult because the random diffusion of photons prevents image formation using direct imaging techniques. If scattered light rejection techniques are used to suppress response to multiple scattering, tomographic reconstruction is still difficult because the percentage of photons which travel relatively straight after initial scattering is very low.

SUMMARY OF THE INVENTION

When coherent light is projected through a scattering medium, the light emerging from the medium is a superposition of a multitude of scattered wavelets, each of which represents a specific scattering path. When this light falls on a diffuse reflecting surface (viewing plane), these wavelets interfere with each other, giving rise to a speckle pattern. By introducing a focused ultrasound pulse into the medium, at any subsequent time as the pulse propagates through the scattering medium, the positions of the scatterers are changed at a corresponding location in the medium—the "probe region"—and this results in a change in the speckle pattern. By considering the changes in the intensities of a large number of speckles during the time when a pulse of ultrasound is traversing the probe region, the light absorption properties of the probe region can be measured, even though multiple scattering interferes with direct imaging of the region. The invention in one of its aspects is directed to this method of imaging in a densely scattering medium. The invention in another of its aspects is directed to apparatus for performing this method of imaging.

BRIEF DESCRIPTION OF THE DRAWING

FIG. 2 is a schematic diagram of a portion of the FIG. 1 imaging system including an interline-transfer charge-coupled device imager and appropriate speckle difference processing circuitry.

DETAILED DESCRIPTION OF THE INVENTION

Figure 1:
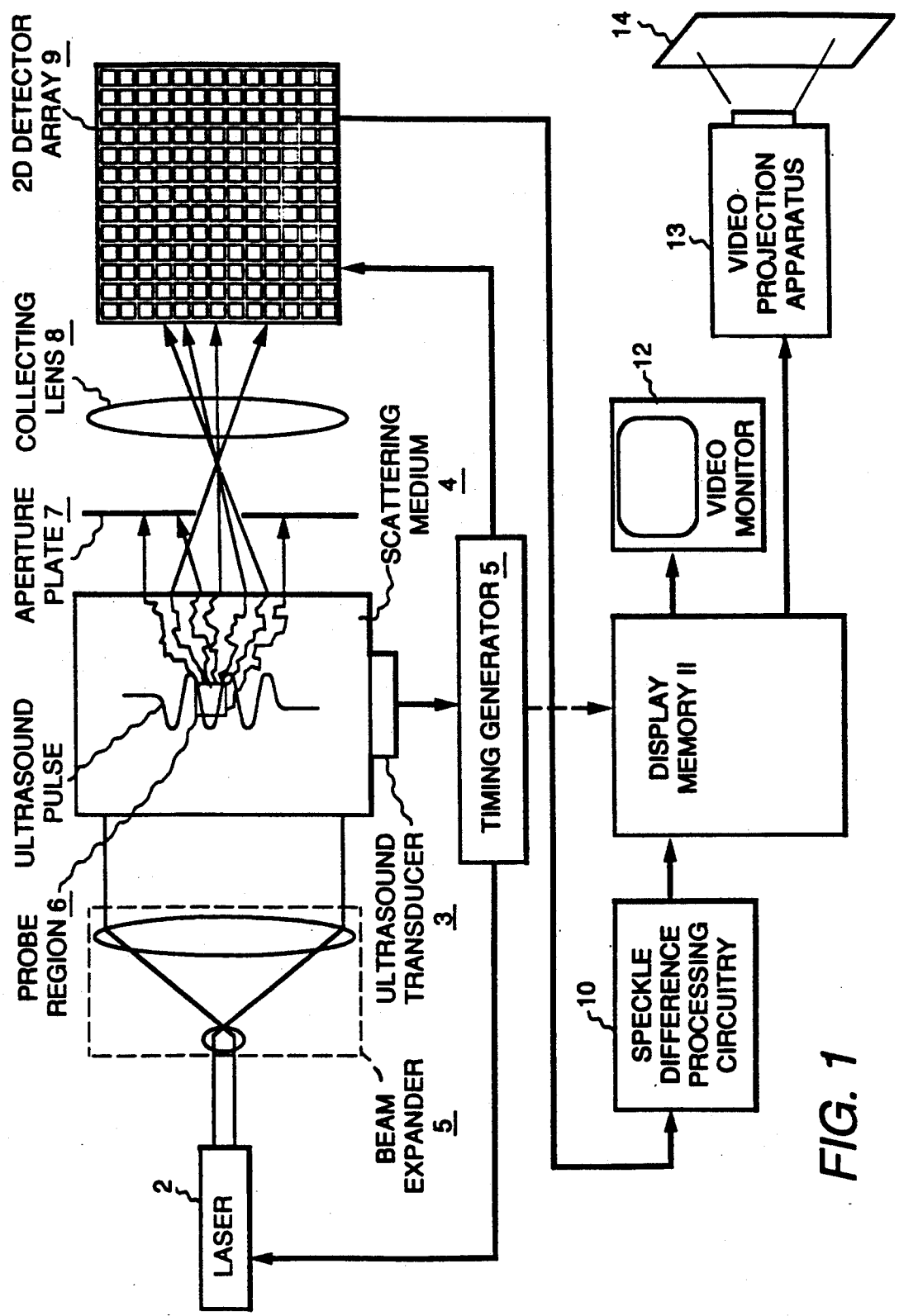
FIG. 1 is a schematic diagram of an imaging system that embodies an aspect of the invention and is used for imaging in a densely scattering medium, in accordance with another aspect of the invention.

The basic elements of the imaging system are shown schematically in FIG. 1 of the drawing. A pulsed laser 2 generates a pulse of light with duration short in comparison to the period of ultrasound emitted from an ultrasonic transducer phased array 3 at the bottom of a scattering medium 4. Light from the laser 2 is directed through a beam expander 5 to project a broad beam (4-6 cm. diameter) of coherent light into the scattering medium 4, to be imaged. In a medical imaging system the scattering medium 4 is living tissue. Functionally, the purpose of the beam expander 5 is to permit large amounts of input light to be utilized without exceeding prudent limits on power density, as might damage the scattering medium 4 (e.g., as might burn living tissue) That is, the largest beam size should be used which is consistent with the geometry of the region to be probed.

Ways in which to construct and operate phased arrays of ultrasonic transducers are known from the art of ultrasonic imaging. U.S. Pat. No. 4,217,684 issued Aug. 19, 1990 to L. S. Smith and A. F. Brisken; U.S. Pat. No. 4,425,525 issued Jan. 10, 1984 to L. S. Smith, A. F. Brisken and M. S. Horner and entitled "ULTRASONIC TRANSDUCER SHADING"; and U.S. Pat. No. 4,460,841 issued Jul. 17, 1984 to L. S. Smith and A. F. Brisken and entitled "ULTRASONIC TRANSDUCER SHADING" describe ways in which an ultrasound beam with a relatively intensified main lobe and relatively attenuated side lobes can be generated. The steering of the beam from a phased array of ultrasonic transducers over 60- to 90-degree sectors is described by C. E. Thomas in U.S. Pat. No. 4,180,790 issued Dec. 25, 1979 and entitled "DYNAMIC ARRAY APERTURE AND FOCUS CONTROL FOR ULTRASONIC IMAGING SYSTEMS". Rather than steering the beam, the fixed-angle beam from a phased array of ultrasonic transducers may be translated, either by mechanically translating the entire array of ultrasonic transducers, or by translating the pattern of electric signals applied to the ultrasonic transducers within their array configuration.

The ultrasonic transducer phased array 3 emits a sonic pulse that travels up through the scattering medium 4, and this pulse is shown schematically by a pressure vs. time doublet pulse at a point in time where the pulse has advanced to the interior of the scattering medium 4. Note that the doublet pulse is temporally short, so its length is confined, and it is focused into a beam such that both transverse dimensions are also small. This means that at any particular moment in time, the ultrasound pulse can be considered to affect significantly only a small volume 6, referred to as the "probe region", within the scattering medium 4.

In general, ultrasound can be characterized either as a longitudinal wave or as a shear wave; and a solid scattering medium will support the transmission therethrough of either type of wave. A liquid scattering medium will, however, support only the transmission of a longitudinal, or pressure, wave therethrough. Inasmuch as the primary application of this invention is in medical imaging and body tissue has a liquid character, the use of longitudinal wave ultrasound is emphasized in the remainder of the application.

Part of the light entering the scattering medium 4 from the beam expander 5 is collected as it leaves the scattering medium 4 by an optical system (shown as comprising an optical aperture 7 and a collecting lens 8, but which may comprise a telescope instead) and is projected onto a two-dimensional light detector array 9. The optical system limits the light acceptance angle of the detector and sets the size of the speckles generated on the two-dimensional detector array 9 from the interference of the light exiting the medium 4. The speckle pattern is a result of the light interference at random phases generated from the scattering of the light in the medium 4. The speckle size is set by adjustment of the optical system to match the size of the pixels in the detector array 9; i.e., the pixels in the two-dimensional detector array 9 must resolve the speckles. By mixing the exit light with a local oscillator beam, optical heterodyne detection can be used to boost the strength of the signal impinging on the detector array 9 to facilitate quantum limited detection, although this procedure is not shown in FIG. 1.

The detector array 9 is of a type that can successively sense at least two successive speckle images formed in response to pulses of light generated by the pulsed laser 2 at times separated by a period of time equal to that between the maximum and minimum peaks of the doublet ultrasound pulse. The absolute change between each pair of corresponding picture elements in the two successive speckle images is determined by speckle difference processing circuitry 10 and the absolute values integrated to generate each output sample supplied from circuitry 10.

Each output sample from the speckle difference processing circuitry 10 is but a single picture element in the complete image of the scattering medium 4. These successive output samples from the speckle difference processing circuitry 10 are written into respective addressed storage locations in a display memory 11. The display memory, once written, can be read repeatedly to generate a video signal suitable for application to a video monitor 12 for direct viewing of the display memory 11 contents. Or the display memory 11 can be read to generate a video signal for application to video projection apparatus 13 used to project an image of the scattering medium 4 onto a photographic film 14 to generate a permanent record of that image. Variants of the exposure of the photographic film 14 to generate a permanent record of that image which are of the nature of contact printing from the face of the video projection apparatus 13 are possible, and other printing methods proceeding from video signals can be used in further embodiments of the invention.

Successive speckle images are subtractively combined and the resulting differences are sent through a non-linear operation (absolute value or square law), and integrated over time and/or space to determine the effect of the ultrasound pulse at a particular location in the scattering medium 4. Since the time of flight of the ultrasound pulse determines its location, and since two samplings of the imager are required to discern the effect of the ultrasound pulse on the speckle pattern, the timing of the ultrasound pulse and the readings of the light detector array 9 are important. The scanning patterns for writing and reading the display memory 11 also affect the mapping into video signal of the speckle difference processing circuitry 10 output signal samples respectively descriptive of the portions of the scattering medium 4 subjected to the effect of the ultrasound pulses. A timing generator 15 is therefore provided to co-ordinate the launchings of ultrasound pulses, the sampling of successive speckle patterns by the light detector array 9, the periodic zeroing of the integrator in the speckle difference processing circuitry 10, the writing of the display memory 11, the reading of the display memory 11, and the supplying of synchronizing pulses to the video apparatus 12 and 13. The design of such timing generators is within the skill of a television electronics design engineer.

The display memory 11 may be written in one set of coordinates and read in another set of coordinates. E.g., the display memory 11 may be written in fan beam coordinates to suit the ultrasonic transducer phased array 3 and read in Cartesian coordinates using phantom raster scanning and pixel interpolating techniques to generate video samples in conventional raster scanning order for the video monitor 12 and the video projection apparatus 13. Such techniques are known from U.S. Pat. No. 4,471,349 issued Sep. 11, 1984 and entitled "PHANTOM RASTER GENERATING APPARATUS SCANNING TV IMAGE MEMORY IN ANGULAR AND ORTHOGONAL COORDINATES", for example.

The display memory 11 may in fact provide two frames of video signal storage, so one frame of video can be scanned one or more times while the other frame is being written, and vice versa. It is generally more convenient to construct the display memory 11 as a random-access memory (RAM) that stores digital signal samples. The digital samples for the RAM can be generated by digitizing the analog output samples of an integrator of analog type within the speckle difference processing circuitry 10, as typically constructed from an operational amplifier with capacitive feedback. This procedure has the advantage that the quantizing errors associated with digitization do not accumulate to affect the integration result. Alternatively, the integrator within the speckle difference processing circuitry 10 may be a digital accumulator for digital signals generated by digitizing the analog differences of the speckle patterns, with the final accumulations before zeroing of the integrator being written to the RAM used as the display memory 11. In still another variant the analog signals descriptive of respective ones of two successive speckle patterns may be digitized before their being subtractively combined. So-called "flash" converters are suitable for the digitization procedures. The video apparatus 12 and 13 use digital-to-analog converters in their input circuitry when the display memory 11 is digital in nature.

The mechanism by which differences in successive speckle patterns will now be considered in greater detail. The reader's attention is directed to the probe region 6 within the medium 4, the light absorption properties of which region are to be measured. Owing to the scattering properties of the medium 4, light passing through the medium 4 takes many different paths before it arrives on the focal plane of the detector array 9. Some fraction of the light passes through the probe region 6, and this fraction contributes to the speckle formation at the focal plane of the detector array 9. If the light scattering properties within the region 6 are altered (owing either to the change in index of refraction induced by the pressure fluctuations of an ultrasound pulse or by the changes in location of the scattering centers induced by such a pulse), the speckle intensities in the focal plane are altered slightly. (Since the phase of the light which passes through the region 6 is changed, the coherent sum at the focal plane will change). The inventors submit that the magnitude of the speckle intensity change on the detector array 9 is a function of the relative light absorption between the probe region 6 and the surrounding medium 4. At one extreme, if all light entering the probe region 6 is absorbed, no speckle change due to compression or expansion of the region 6 will be observed since there will be no light passing through the probe region 6 and falling on the detector. At the other extreme, if the probe region 6 has low light absorption compared with the surrounding medium, the fraction of light from the region contributing to speckle formation will be relatively high and will produce a greater speckle intensity change from the corresponding phase change in the probe region 6. Regions of high absorption contrast that are located elsewhere will have little effect since this contrast is rapidly smeared out by scattering. Thus, any contrast that is observed can be attributed to absorption contrast very close to the region where the ultrasound pulse was at the time the observation was made.

To produce the compression/expansion (and/or vibration) at the probe region 6, an ultrasound transducer 3 is used to project a focused ultrasound pulse into the medium. The spatial extent of the ultrasound pulse at the focus point defines the probe region 6. A timing controller within the timing generator 15 is programmed to cause the laser 2 to fire two laser pulses into the medium 4, one when the leading lobe of the doublet ultrasound pulse is at the probe region 6, and another when the pulse has travelled one-half an ultrasound wavelength through the medium 4 so the trailing lobe of the doublet ultrasound pulse is at the probe region 6. The timing generator 15 supplies scanning signals to the two-dimensional detector 9 that condition it to acquire two successive speckle images from the corresponding laser pulses. Because the ultrasound pulse produces compression and expansion (and/or vibration) of the probe region 6 as it travels through the medium 4, the speckle pattern changes between the two laser exposures. The differences between corresponding pixels in the two successive speckle images are read from the two-dimensional detector 9 and the average speckle intensity change between detector exposures is calculated by the speckle difference processing circuitry 10. The magnitude of this result is a function of the light absorption at the probe region 6, the compressability of the tissue, and the acoustic power at the probe region 6.

Because there is no requirement for light to travel in a straight line from the light source through the scattering medium to the detector, a system using the invention is expected to have a signal-to-noise advantage over a system using one of the prior art techniques. In a system using the invention, light can travel from the source to the probe region by any path, and travel by any path from the probe region to the detector. This capability allows the signal level to be increased by each of two means. The source illumination can be a broad beam, which increases the light fluence at the probe region without exceeding a maximum power/area figure for the medium, and a large area detector can be used to collect more light exiting from the medium. The signal-to-noise ratio at a pixel within the two-dimensional detector array 9 is set by the ratio of the received light power that passed through the probe region 6 to the square root of the received light power that did not pass through the probe region 6, and not by the exponential loss governed by the large scattering coefficient as in "straight light systems".

Also, averaging the signal over many pixels in the two-dimensional detector array 9 can result in up to a square-root-of-N improvement in signal-to-noise ratio, where N is the number of pixels. To get close to a square-root-of-N improvement in signal-to-noise ratio, the speckle information contained in each pixel must be substantially independent from that contained in an adjacent pixel. That is, the photodetectors in the rows and in the columns of the two-dimensional detector array 9 must have a pitch similar to speckle diameter to get the full improvement.

FIG. 2 shows the detector array 9 as comprising a micro-channel plate 91 and an interline-transfer charge-couple-device (CCD) imager 92. The micro-channel plate 91 is operated as an electrically controlled shutter between the collecting lens 8 and the CCD imager 92, which shutter allows the passage of light generated by pulsing the laser 2 first and second times. The photodetectors in the interline-transfer CCD imager 92 convert the speckle pattern generated by the first pulse from laser 2 to a field of charge packets, and the transfer gates of the imager 92 are biased to allow those charge packets to dump into the masked interline CCD registers of the imager 92 as soon as those charge packets are generated. During the time between the first and second pulses from laser 2, the potential applied to the transfer gates is changed to erect a barrier to flow of charge between the photodetectors and the masked interline CCD registers. The photodetectors in the interline-transfer CCD convert the speckle pattern generated by the second pulse from laser 2 to another field of charge packets, after which the micro-channel plate 91 is conditioned to no longer allow the passage of light. The interline-transfer CCD acquires in a very short time interval two successive speckle images for storage.

The samples of the speckle pattern generated by the first pulse from laser 2 stored as respective charge packets in the masked interline CCD registers of the imager 92 are read out serially a line at a time from those CCD registers to a charge-sensing amplifier in the imager 92, which charge-sensing amplifier generates corresponding voltage samples as sampled-data analog output signal from the imager 92. These sampled-data analog voltage samples are digitized by an analog-to-digital converter 101, which may be of the so-called "flash" type and is included in the speckle difference processing circuitry as shown in FIG. 2. The digitized samples of the speckle pattern generated by the first pulse from laser 2 are stored in respective storage locations within a field storage memory 102, which memory 102 is included in the speckle difference processing circuitry as shown in FIG. 2.

After the samples of the speckle pattern generated by the first pulse from laser 2 have been stored in the field storage memory 102, the transfer gates of the imager 92 are biased to allow the charge packets stored in its photodetectors to dump into the masked interline CCD registers of the imager 92. These charge packets describe samples of the speckle pattern generated by the second pulse from laser 2. The transferred charge packets are then read serially a line at a time from those CCD registers to the charge-sensing amplifier in the imager 92, which charge-sensing amplifier generates corresponding voltage samples as sampled-data analog output signal from the imager 92. These sampled-data analog voltage samples are digitized by an analog-to-digital converter 101.

Memory 102 is operated to provide the delay necessary to align temporally digitized samples of the speckle patterns generated responsive to the first and second pulses from laser 2 that correspond with each other inasfar as their spatial locations in their respective speckle patterns are concerned, and each successive pair of corresponding samples is differentially combined in a digital subtractor 102. The digital difference output signal from the subtractor 102 has its absolute value determined, for application as input signal to a digital accumulator 104. The designs for some digital subtractors provide for automatically subtracting the smaller of their inputs from the larger of their inputs to obtain a difference signal that is always positive.

FIG. 2 presumes the subtractor 102 to be of a type that generates a signed difference signal in two's complement form, requiring an absolute-value circuit 105 following the subtractor 102 to generate the input signal for the digital accumulator 104. The absolute-value circuit 105 conventionally comprises a rank 106 of two-input exclusive-OR gates receiving respective ones of the (n−1) least significant bits of the n-bit difference signal from the subtractor 102 as respective first input signals and receiving the most significant, sign bit of the n-bit difference signal as respective second input signals. There is a shift 107 of the most significant, sign bit of the n-bit difference signal to the least significant bit position with ZERO-filling of the more significant bit places to generate a summand for application to a digital adder 108. The digital adder 108 receives as the other of its summands the responses of the exclusive-OR gates in the rank 106, with bit place order preserved. The sum output signal from the digital adder 108 is supplied as the output signal of the speckle difference processing circuitry 10 in FIG. 2 and is a measure of the average of the absolute-value speckle intensity change between detector array 9 exposures.

When imaging a two-dimensional slice, one can take advantage of the fact that the ultrasound pulse is propagating through the scattering medium 4 and condition the laser pulse sequence more than once during the time of flight of the ultrasound pulse. When using a single two-dimensional light detector array 9 for mapping the entire image plane, the interval between conditioning the laser 2 to generate its double pulse sequence must be sufficiently long to allow reading out all the speckle pattern samples stored in the detector array 9. When using a single two-dimensional light detector array 9 for mapping the entire image plane, there is no need for shuttering the detector array 9, so long as the detector array 9 is irradiated only with energy generated by pulsing the laser 2.

Accordingly, the micro-channel plate 91 may be dispensed with, unless its light amplification properties are desired. The light amplification properties of the micro-channel plate 91 are useful in reducing the energy required for obtaining usable images using transillumination, reducing the likelihood of burning tissue used as the scattering medium 4.

The electrically controlled shuttering the micro-channel plate 91 provides is useful when a plurality of the two-dimensional detector arrays 9 are arrayed for selectively receiving speckle patterns generated responsive to respective successive pairs of light pulses in a continuous stream of light pulses from the laser 2. A multiple-imaging lens can be used in the collection optics to apportion transillumination amongst the two-dimensional detector arrays 9. As much as an entire line of data can be acquired each time an ultrasound pulse is launched, each of the two-dimensional detector arrays 9 detecting a respective spatial phasing of the probe regions 6 in the line. The line imaged by this technique can be scanned through the medium 4, either mechanically or with a phased-array of ultrasound transducers, to generate a digital representation of a two-dimensional slice or a digital representation of a three-dimensional solid.

By using one photodetector to acquire charge packets descriptive of corresponding spatial locations in the successive speckle patterns, as previously described, the dark current of the photodetector cancels out in the process of differentially combining successive speckle patterns. One can avoid the need for the plurality of field storage memories 102 respectively associated with a plurality of two-dimensional detector arrays 9 for detecting different probe-region spatial phasings. This can be done by differentially combining successive speckle patterns as detected by separate ones of the plurality of two-dimensional detector arrays 9, thereby greatly reducing the delay needed for temporal alignment of samples having corresponding spatial locations in the successive speckle patterns. The problem with this approach is that errors in the matching of photoresponses of the correspondingly located photodetectors in the imagers, as caused by differences in dark currents or photodetection sensitivity slopes, are integrated and may adversely affect the uniformity of the imaging by transillumination. Using correction factors stored in digital memory to compensate for effects similar to these is known in the art, but can require memory comparable in size to that in the discarded plurality of field storage memories 102. Using different types of two-dimensional light detector array 9 is a more promising way to reduce the size of the memory used to align temporally digital samples descriptive of corresponding spatial locations in the successive speckle patterns.

For example, each interline-transfer imager used in the system can be modified, so that the transfer gate for each line of photodetectors is biased after the charge packets descriptive of the first speckle image have been clocked out of the associated CCD interline register, to permit transfer of the charge packets descriptive of the second speckle image from the line of photodetectors to that CCD interline register. The respective lines of the first and second speckle images are read out on a line-interleaved basis and a line storage memory is used to replace the field storage memory 102 in a modification of the speckle difference processing circuitry 10 of FIG. 2. The absolute values of only every other line of the digital subtractor 103 output signal are supplied to the digital accumulator 104 in this modification of the speckle difference processing circuitry 10 of FIG. 2, the samples in the intervening lines being replaced by arithmetic zeroes in the accumulation or not being accumulated.

As a further example, each interline-transfer imager used in the system can be modified to provide masked CCD interline registers each having two successive storage locations for each photodetector in the associated line of photodetectors, to only alternate ones of which storage locations the charge packets descriptive of a line of samples of speckle image can be transferred. After the charge packets descriptive of the first speckle image have been transferred to these alternate storage locations, the charge packets in the CCD interline registers are clocked ahead one stage. Then the charge packets descriptive of the second speckle image have been transferred to these alternate storage locations, to interleave the speckle images on a pixel-by-pixel basis in the CCD interline registers. The respective lines of the first and second speckle images are read out on a pixel-interleaved basis and a one-sample delay replaces the field storage memory 102 in a modification of the speckle difference processing circuitry 10 of FIG. 2. The absolute values of only every other digital subtractor 103 output signal are supplied to the digital accumulator 104 in this modification of the speckle difference processing circuitry 10 of FIG. 2, the intervening samples being replaced by arithmetic zeroes in the accumulation or not being accumulated.

As a still further example, each interline-transfer imager used in the system can be modified to provide two masked CCD interline registers for each line of photodetectors, one interline register to which the charge packets descriptive of a line of samples of the first speckle image is transferred and another interline register to which the charge packets descriptive of a line of samples of the second speckle image is transferred. Provision is made for reading the two interline registers out in parallel to a differential charge-sensing amplifier that is the output stage for this modification of the interline-transfer imager. The sampled-data analog output samples from the differential charge-sensing amplifier are rectified and digitized, or are digitized and the absolute values taken, to generate input signal samples for a digital accumulator much like digital accumulator 104. Recovery time for this modified imager is half that for the unmodified interline transfer CCD imager because the two speckle images are clocked out in parallel, rather than one after the other.

The invented imaging method relies on the fact that the tissue to be imaged has good ultrasound propagation characteristics. It should work well in areas such as the breast and abdomen where ultrasound imaging works well. It may prove to be complementary to traditional ultrasonic imaging for two reasons:

1) it measures a different tissue property—namely, optical absorption versus acoustic impedance change—and 2) the ultrasound does not have to make a round trip, but only needs to travel one way.

What is claimed is:

1. A method for imaging portions of a scattering medium disposed between first and second opposed surfaces thereof, said scattering medium being transmissive of ultrasound pulses, said method comprising the steps of:

propagating ultrasound pulses through said scattering medium in a direction substantially parallel to each of said first and second surfaces;

irradiating the first surface of said scattering medium with a coherent beam of radiant energy, which said scattering medium at least partially disperses;

projecting onto a focal plane an image of the radiant energy exiting the second surface of said scattering medium, thereby to form speckle patterns of radiant energy;

detecting the speckle patterns projected on said focal plane, so as to resolve individual elements of said speckle patterns;

sensing the difference in levels of detected energy in the corresponding individual elements of pairs of successive said speckle patterns to generate electrical signal representations of those differences; and integrating the electrical signal representations of the differences in levels of detected energy in the corresponding individual elements of pairs of successive said speckle patterns to generate electrical signal representations of respective images of the portions of said scattering medium through which an ultrasonic pulse travels.

2. A method as set forth in claim 1 for imaging portions of a scattering medium, said method including the further step of:

writing the electrical signal representations of respective images of the portions of said scattering medium through which an ultrasonic pulse travels into an electronic memory.

3. A method as set forth in claim 2 for imaging portions of a scattering medium, said method including the further steps of:

reading the electrical signal representations of imaged portions of said scattering medium to a video monitor; and displaying on a screen of said video monitor the imaged portions of said scattering medium.

4. A method as set forth in claim 2 for imaging portions of a scattering medium, said method including the further steps of:

reading the electrical signal representations of imaged portions of said scattering medium to video projection apparatus; and generating a photographic record of the imaged portions of said scattering medium as projected by said video projection apparatus.

5. A photographic record generated by the method set forth in claim 4.

6. Apparatus for imaging portions of a scattering medium disposed between first and second opposed surfaces thereof, said scattering medium being transmissive of ultrasound pulses, said apparatus comprising:

ultrasound transducer apparatus for propagating ultrasound pulses through said scattering medium in a direction substantially parallel to each of said first and second surfaces;

apparatus for irridiating the first surface of said scattering medium with a coherent beam of radiant energy which said scattering medium at least partially disperses;

optics for projecting onto a focal plane the radiant energy exiting the second surface of said scattering medium, thereby to form speckle patterns of radiant energy;

a two-dimensional detector array located for detecting the speckle patterns projected on said focal plane, said detector array having detector elements spaced so as to resolve individual elements of said speckle patterns;

means for sensing the difference in levels of detected energy in the corresponding individual elements of pairs of successive said speckle patterns to generate electrical signal representations of those differences; and means for integrating the electrical signal representations of the differences in levels of detected energy in the corresponding individual elements of pairs of successive said speckle patterns to generate electrical signal representations of respective images of the portions of said scattering medium through which an ultrasonic pulse travels.

7. Apparatus as set forth in claim 6 for imaging portions of a scattering medium, which apparatus further includes:

an electronic memory arranged to be written in response to said electrical signal representations of respective images of the portions of said scattering medium through which an ultrasonic pulse travels and to be read from in raster scan order to provide a video signal descriptive of the imaged portions of said scattering medium.

8. Apparatus as set forth in claim 7 for imaging portions of a scattering medium, which apparatus is operated in combination with:

a video display monitor connected for generating a display of the imaged portions of said scattering medium responsive to the video signal read from said electronic memory.

9. Apparatus as set forth in claim 7 for imaging portions of a scattering medium, which apparatus is operated in combination with:

video projection apparatus for projecting an image of the imaged portions of said scattering medium onto a photographic medium.

* * * * *